United States Patent [19]

Kalnberz et al.

[11] 4,089,071
[45] May 16, 1978

[54] MATERIAL FOR MAKING BONE ENDOPROSTHESIS AND ENDOPROSTHESIS MADE OF SAID MATERIAL

[76] Inventors: Viktor Konstantinovich Kalnberz, ulitsa Stendera, 13, kv. 2; Kharald Arnoldovich Yanson, ulitsa Tereshkovoi, 31a, kv. 88; Ivar Valterovich Knets, ulitsa Ezermalas, 20, kv. 4; Jury Zhanovich Saulgozis, bulvar Imanta, 22, kv. 26, all of Riga, U.S.S.R.

[21] Appl. No.: 721,406

[22] Filed: Sep. 8, 1976

[51] Int. Cl.² .............................................. A61F 1/24
[52] U.S. Cl. ...................................... 3/1.9; 128/92 C; 428/222; 428/230; 428/247
[58] Field of Search .................................. 3/1.9–1.913; 128/92 C, 92 CA, 92 R, 92 G, 334 R; 428/222, 230, 231, 247

[56] References Cited

U.S. PATENT DOCUMENTS

| 3,662,405 | 5/1972 | Bortz et al. ................................. 3/1.9 |
| 3,683,422 | 8/1972 | Stemmer et al. ...................... 3/1.9 UX |
| 3,886,600 | 6/1975 | Kahn et al. ........................ 3/1.91 UX |
| 3,893,196 | 7/1975 | Hochman .................................. 3/1.91 |
| 3,992,725 | 11/1976 | Homsy .................................. 3/1.9 X |

FOREIGN PATENT DOCUMENTS 2,502,884 7/1976 Germany ................................... 3/1.9

OTHER PUBLICATIONS

Quartz and Graphite Filament Reinforced Polymer Composites for Orthopedic Surgical Application, by S. Musikant, Journal of Biomedical Materials Research Symposium, vol. 1, 1971, pp. 225–235.

Primary Examiner—Ronald L. Frinks
Attorney, Agent, or Firm—Steinberg & Blake

[57] ABSTRACT

A material for making a bone endoprosthesis having a reinforcing base composed of nets which are made of a chemically and biologically inert metal and elastic polymeric material. The entire space confined within the nets is occupied by the binder doped with an antiseptic, the volumetric ratio between the metal nets and the entire material being selected such that the modulus of elasticity of the material approximates that of the bone tissue to be replaced.

An endoprosthesis of the invention is cross-sectionally shaped as a row of spirals made of the proposed material and interlinked through an element made of the same network material, while the entire space between the prosthesis components is embedded in the binder. In an embodiment of the present invention, the endoprosthesis has a spiral sheath made of the proposed material. The interior space of the sheath accommodates several spirals, each comprising a number of spirals interlinked by the element made of the proposed network material.

13 Claims, 13 Drawing Figures

MATERIAL FOR MAKING BONE ENDOPROSTHESIS AND ENDOPROSTHESIS MADE OF SAID MATERIAL

The invention relates generally to the art of medicine and more specifically it is concerned with an improvement in constructional materials used for making endoprostheses that find application in traumatological and orthopedical practice as implants to replace defective bone fragments.

The present invention can most advantageously be used for treatment of traumatic lesions of large bones of extremities, as well as for permanent or temporary replacement of bone defects following an operative removal of osseous neoplasms, in spontaneous osteolysis or after a considerable elongation of extremital bones.

Known in the present state of prosthetic surgery are a number of combinations of diverse materials used as implants or as a stock material for making artificial bones.

All the heretofore-known materials for making bone endoprostheses may be divided into three basic groups: metals, ceramics and polymers. In addion, a variety of combinations thereof are now in use. Metals, such as titanium, stainless steel, cobalt, as well as endoprostheses made therefrom prove to be too heavy, hard-to-unite with the fragments of live bone, their modulus of elasticity is by an order higher than that of bone which results in local osteolysis at the joints of bone tissue with the endoprosthesis and overstressing the endoprosthesis due to its excessive rigidity. It is corundum $Al_2O_3$ that has most commonly been used in experiments on animals (cf. L. Cini et al., Chirurgia Org. movim., 1972, vol. 60, No. 4, pp. 423–430; D Geduliding et al., Astracts SIGOT XIII World Congress, Copenhagen 1975, p. 75; S. Hulbert et al., J. Biomed. Mater. Res., 1970, vol. 7, pp. 433–456, G. Heimke et al., Berichts Dtschr. Keram. Ges., 1973, 50 Kongress, S.4–8; V. Hall, J. Biomed. Mater. Res., 1972, part I, pp. 1–4); among commonly employed other materials there may be cited the following:

glass carbonate (cf. J. Benson, J. Biomed. Mater. Res., 1972, part I, pp. 41–47; J. Colette et al., J. Bone Surg., 1971, vol. 53-A, No. 4, pp. 799–800; C. Staniski et al., J. Biomed. Mater. Res., 1973, vol. 7, No. 3, pp. 97–108);
caclium aluminate (cf. C. Hall, Bioceramics Engineering in Medicine, J. Wiley & Sons Inc., 1972, 479 p.; G. Graves et al., J. Biomed, Mater. Res., 1972, part I, pp. 91–115; S. Hulbert et al., J. Biomed. Mater. Res., 1970, vol. 7, pp. 433–456; Ch. Homsy et al., Clinical Orthopaedics, 1972, No. 89, pp. 220–235);
glass ceramics (cf. B. Blencke et al., Zschr. Orthop. 1974. Bd. 112, S. 978–980; L. Hench et al., J. Biomed. Mater. Res., 1973, vol. 7, No. 3, pp. 25–42; G. Piotrowski et al., Proceed. 6th Annual Internat. Biomater. Sympos., Clemson, 1974, USA);
pure carbon (cf. Ch. Homsy et al., Clinical Orthopaedics, 1972, No. 89, pp. 220–235; J. Benson, J. Biomed. Mater. Res. 1972, part I, pp. 41–47).

One must consider porous materials as more promising, since their use makes it possible to reduce the modulus of elasticity of the bone endoprosthesis and facilitate the union of the latter with live bone fragments. Bone prostheses were made, in this case, by press-moulding of powdered metal (cf. Nilles J., Lapitsky M., CA, J. Biomed. Mater. Res., 1973, vol. 7, No. 3, pp. 63–84), or from short lengths of titanium wire subjected to sintering at high pressure and temperature in a vacuum (cf. Galante J. et al., CA, J. Biomed. Mater. Res., 1973, vol. 7, No. 3, pp. 43–61).

The elastic strain featured by the aforesaid materials lies within 2 to 4% of the breaking strain, its modulus of elasticity being seven-fold inferior to that of compact bone tissue. Among materials of that type, porous press-moulded titanium having a specific gravity of 3.4 g/cm$^3$ and a porosity of 75% that was optimum.

In 1971, "Dr. Ing. Reinhard Straumann A.G." was granted a patent for a Ti-Zr alloy (cf. French Pat. No. 2,101,599 Cl. A61b17/00), both components being in equal amounts. Said material exhibits high corrosion resistance and has a relatively low modulus of elasticity.

All the afore-mentioned materials are isotropic and as to their deformability, specific deformation energy criterion, modulus of elasticity and specific gravity, they differ widely from the respective, parameters of compact osseous tissue, i.e. they are far from keeping with the properties of the natural bony material they are to replace. Ceramic materials are distinguished for high compression strength, chemical and biological inertness, porous structure but, on the other hand, feature low resistance to impact loads, are brittle and liable to break when tensioned.

Apart from the materials specified above, there have been proposed and studied some compounds that would gradually be replaced by natural tissues. It is worth citing among such materials one of pressed flour-apatite crystals (cf. S. Levitt et al., J. Biomed. Mater. Res., 1969, vol. 3, pp. 683–684), as well as complex calcium-oxide and aluminum-oxide compounds (cf. G. Graves et al., J. Biomed. Mater. Res., 1972, part I, pp. 91–115), or porous calcium phosphate.

Even the most promising material of that group, viz., aluminium oxide (corundum) which is biologically inert and strong enough when brazed, has proved to be unsuitable for replacing major defects of diaphyseal bones that are subject to daily repeated impact loads, since it is easily destructible on account of being brittle. Higher resistance to dynamic loads is offered by a material of the Cerosium type (cf. L. Smith et al., Archives of Surg., 1963, vol. 87, pp. 653–661; L. Smith et al., J. Bone & Joint Surg., 1964, vol. 4 - A, No. 5, p. 1155) which is, in effect, porous corundum impregnated with a more viscid component, viz., epoxy resin. However, as studies have shown, an endoprosthesis made of Cerosium loses up to 45 percent of its initial strength as early as after six months in the organism, this being due to fine porosity of this material and its poor adhesibility to the surrounding tissues.

Similar disadvantages are inherent in the bone substitute disclosed in U.S. Pat. No. 3,713,860; Cl. 3–1, and in French Pat. No. 2,106,242; Cl. A 61fI/00, which is essentially a ceramic base impregnated with pure methyl-methacrylate and coated with a positive polymer layer. Use is also made in medical practice of polyethylene acrylate as a bone substitute (cf. J. Scales et al., 1965, in Biomechanics and Bioengineering Topics, Oxford, Pergamon Press).

However, these materials also proved to be inadequately strong. One more process for producing a material for bone prosthesis from plastisol by its foaming and repeated heat treatment has been developed at the Kiev Prosthesis Plant (cf. USSR Inventor's Certificate No. 380,321, 1971).

A number of various combinations of prosthetic materials are now in use, such as:

- a metal rod with a porous coating deposited on its surface to cover it at least partially (cf. French Pat. No. 2,095,854 entitled "Element de prothese chirurgicale", Cl. 61fI/00;
- a titanium or titanium-alloy material with a coating of oxide, nitride, carbide or carbonitride deposited to prevent wear and corrosion of the implant (cf. U.S. Pat. No. 3,643,658 entitled "Implants of Titanium or Titanium Alloy for the Surgical Treatment of Bones", Cl. 128-92);
- an implant made of graphite and boron fibres coated with silicone (cf. French Pat. No. 2,104,069 entitled "Matiere destinee a la realisation d'implants", Cl. A 61fI/00);
- a spongy ceramic bone prosthesis adapted for tissue fluid to flow therethrough, featuring its outer layer as a composite rigid-base material (cf. U.S. Pat. No. 3,662,405 entitled "Reinforced Porous Ceramic Bond Prosthesis", Cl. 3-1);
- a material which is essentially porous alumina impregnated, prior to being press-moulded, with a methyl-meth-acrylate monomer polymerized under the effect of gamma-rays (cf. French Pat. No. 2,106,242; Cl.A61fI/00; U.S. Pat. No. 3,713,860 Cl.3-1; British Pat. No. 1,314,468; Cl.ABR);
- an implantable bone prosthesis made as a metal rod coated with plastics (cf. French Pat. No. 2,204,392 Cl.A61fI/00 granted to the Swiss firm "sulzer Freres");
- a bone prosthesis adapted to function under heavy load conditions (cf. U.S. Pat. No. 3,683,422; 3-1), which comprises a rigid reinforcing element and a fibrous or textile material impregnated with an elastomer and coating said reinforcing element. In one of the embodiments of said invention, a cam-like reinforced fibrous elastomer element is attached to one of the ends of the reinforcing element; a coating of a textile with open pores allowing intergrowth of body tissues is applied to the elastomer-lined surface of the reinforcing element facing the live bone. The fibrous and textile components of the prosthesis are preferably made of Dacron, while silicone rubber is used as the elastomer, and Dacron velour as the textile.

Although the above prosthesis is the most perfect one among the heretofore known borne prostheses, its modulus of elasticity is much inferior to that of compact osseous tissue.

There is likewise known a composite material replacing bone defects, comprising epoxy resin reinforced with randomly arranged gypsum or quartz particles. Its modulus of elasticity is of the same order as that of a live bone when under a load imposed lengthwise thereupon.

However, all the heretofore known materials and endoprostheses made therefrom meet but partially the requirements imposed on bone prostheses both chemically and biologically inert. In some cases, said materials and endoprostheses satisfy the requirements as to compression strength, while a number of these have a porous surface so as to enable the surrounding tissues to grow thereinto. As a rule, when developing endoprostheses, no account is taken of the biomechanical characteristics and conditions of loading of the natural materials of osseous tissue and the natural structure of diaphyseal bones as a whole. On the other hand, some other materials possess higher specific gravity as compared to natural bone, are more brittle and less resistant to cyclic and impact loads, and feature an inadequate power capacity while under load. Homogeneous or isotropic nature of implantable materials hampers the applicability of the prior-art endoprostheses as a component of the natural biomechanical system, such as the shin and thigh, wherein the endoprosthesis would be enabled to function as the normal bone. The latter prerequisite is quite substantial inasmuch as only with that fully satisfied the endoprosthesis would be efficiently protected by natural adaptive mechanisms when exposed to high cyclic loads. As a rule, none of the hitherto used endoprostheses or materials for bone prosthetics exhibits stress-adaptation or theological-adaptation features, nor are said endoprostheses adequately acted upon by the muscles as external active tensors, and by the ligaments and fasciae as external passive tensors. All the aforementioned factors taken together might be instrumental in raising the actual margin of safety of an endoprosthesis by a factor of three. This, however, becomes practicable only with such a material and such a construction of endoprosthesis that would fall into closer concordance with the elastic behaviour and deformability of natural bone tissue and with those of the whole bone to be replaced with an artificial analogue.

It is an object of the present invention to provide a material for making bone endoprostheses such as would approximate to a maximum extent the human bone tissue as far as the mechanical characteristics thereof are concerned.

Another object of the present invention is to provide an endoprosthesis from the proposed material, that would imitate to a maximum extent the bone to be replaced as to its structure and properties.

Still another object of the invention is to prolong the effective life of a bone endoprosthesis in the human organism.

Yet another object of the invention is to render the proposed bone endoprosthesis more resistant to impact and cyclic loads.

An additional object of the invention is to provide an endoprosthesis that will make use of the natural protective and adaptive reactions of human organism to mechanical stresses inherent therein.

These and other objects are accomplished by that in a material for making bone endoprostheses, comprising a reinforcing base and a binder containing an anticeptic, the reinforcing base is, according to the invention, made as a number of nets, some of which are made of a chemically and biologically inert metal or alloy while the other nets are made of a chemically and biologically inert elastic polymeric material, whereas the inter-net space is filled with the binder, and the volumetric ratio of the metal nets to the entire material is selected such that the modulus of elasticity of the material approximates that of the bone tissue to be replaced.

The material proposed herein provides for a most uniform stress distribution between individual components thereof, which is a paramount prerequisite of its durability. Mechanical stresses exerted upon the contact surface between the implant and the bone are taken up by the binding agent and further transmitted to the reinforcing members of the composite material by virtue of adhesion of the binder to the reinforcing members. Provision for two types of reinforcing nets made of a chemically inert metal or alloy and of an elastic polymeric material ensures uniform redistribution of stresses throughout the bulk of the implant and conduces to better cohesion between the reinforcing base and the binder when under mechanical stresses.

It is desireable that the metal net be made of a chemically and biologically inert metal, viz. titanium or its alloys.

The basic advantage of such a net is its relatively low modulus of elasticity and volume weight compared to some other metals, such as steel and cobalt. This imparts high strength to the entire endoprosthesis with the optimum flexural and torsional rigidity (corresponding to that of the bone being replaced) remaining unaffected. Application of a net made from titanium or alloys thereof enables the specific gravity of the composite material to be maintained equal to about 2 g/cm$^3$.

It is also desireable that the wires of the nets form parallelogram-shaped meshes with the acute angle thereof equal to 60°.

Such an arrangement of the wires in the nets provides for an optimum resistance of the implant to shear in the plane of reinforcement thereof. This also ensures such anisotropy of the implant elastic characteristics that corresponds to that of the real bone tissue. Moreover, such a net configuration ensures good damping of dynamic loads applied along the implant longitudinal axis.

The wires of the nets may be set apart at a maximum angle of 10° in parallel planes.

This contributes to a uniform distribution of tangential stresses throughout the bulk of the implant and provides optimum operating conditions for the binding agent when a load is applied to the implant.

The volumetric ratio between the metallic nets and the entire composite material should preferably be within 1:5 to 1:3.

This ensures a higher degree of deformation of an endoprosthesis made from the proposed material in response to a load applied thereto as compared to the commonly known bone endoprostheses. It is owing to the afore-specified volumetric ratio between the metal nets and the entire material that an endoprosthesis made therefrom is deformable like normal bone tissue, thus providing for a reasonable joint action of the system bone-implant. In addition, the given volumetric content of the metal reinforcing structures in the herein-proposed composite material imparts adequate strength and rigidity to the implant while retaining the low volume weight thereof.

It is advisable that epoxy resin with a curing agent may be used as the binder. The proposed binding agent enables production of a composite material featuring higher elastic behaviour, deformability and strength characteristics.

Moreover, said binder may be polyethylene with graphite as a filler. Such a binder offers higher resistance to cracking and is more resilient than an epoxy resin-based binder.

In an embodiment of the present invention, an endoprosthesis made of the herein-proposed material is cross-sectionally a plurality of rows of spirals made from said material, the spirals of each row being interlinked through an element made of a network material and adapted to embrace all the spirals of the row, while all the endoprosthesis components are embedded in a binding agent.

This provides for optimum functioning of the endoprosthesis under normal physiological conditions. Spirals made from the proposed material are the principal elements adapted to take up compression and tensile stresses, while the spirality of said elements is similar to that present in a real bone. The additional element that embraces all the spirals of a row is in effect the principal element that is to take up shearing stresses resulting from twisting of the endoprosthesis. The binding agent is to fix the position assumed by the spirals in the endoprosthesis and redistribute stresses among individual spirals, as well as between the spirals and the additional element which embraces the latter in each of the rows.

Hand of spiral winding in adjacent spirals of each row may alternate.

Such alternation of the hand of spiral winding ensures a uniform load distribution throughout the entire bulk of the endoprosthesis.

This alternating spiral structure operates most efficiently under dynamic loads whereto the bone is exposed most of the time.

According to one of the embodiments of the invention, the centres of all the spirals in each row lie on a common imaginary straight line.

Thus, better interlinking of the rows of spirals is attained and fairly high resistance to shear stresses is imparted to the endoprosthesis.

It is advantageous that the endoprosthesis of the thigh bone be made as a spiral sheath whose interior accommodates a number of spirals arranged lengthwise said sheath, the perimeter of each of the spirals being less than that of the sheath, each of said spirals being cross-sectionally a row of spirals made of said composite material and interlinked through a common element made of the same material, whereas a bearing rod is provided in the central zone of said sheath and all the components of the prosthesis are embedded in a binder.

The outer spiral sheath is to take up shear stresses and translate these, via the binding agent, to the spirals laid inside the endoprosthesis, while the rigid bearing rod ensures firm interconnection of the endoprosthesis with the means for attaching it to the bone.

In the endoprosthesis of the tibial diaphysis, the cross-sectional shape of the sheath resembles an oblique-angled triangle, while the spirals of the herein-proposed material are located at the vertices of said triangle.

The triangular cross-sectional shape of the endoprosthesis ensures an optimum ratio between the weight and size thereof when the prosthesis is exposed to flexural or torsional strain. In addition, due account is made of the fact that the shin and fibular bones along with some related muscles establish such a biological system that involves a triangular cross-sectional shape of the endoprosthesis, which is optimum. The spirals serve as the principal elements adapted to take up compression, tensile and shear stresses that arise in the sheath of the endoprosthesis as a result of torsional straining of the latter.

In an embodiment of the present invention, the spiral located at the vertex of the smaller angle of the triangle, is wound in a direction opposite to that of the spirals located at the other vertices of the triangle.

When under dynamic loads, the spirals work as an inner damper of the endoprosthesis. In this case, the opposite hands of winding of the spirals contribute to higher resistance to flexure and torsion when the endoprosthesis sustains buckling or oblique-flexure strain, i.e., when under conditions wherein conventional endoprostheses are most likely to buckle or cripple.

The construction of the endoprosthesis renders it possible to make use of the natural mechanisms of the tibial bone for adaptation to physiological loads.

Each of the spirals enclosed in the outer sheath may be composed of a number of spirals of a smaller diameter, twisted together.

Such a construction provides for an optimum system adapted to absorb energy in the process of straining the endoprosthesis. Each of the composite spirals is free to twist when exerted by a bending or tensile force and, besides, contracts so as to offer better resistance to tension. When compressed, the spiral gets additionally untwisted, hence elongated so as to exhibit higher resistance to compression. The system works especially efficiently at relatively low variable loads.

Further objects and advantages of the present invention will become clearly understood from a detailed description of some illustrative embodiments thereof to be considered in conjunction with the accompanying drawings, wherein.

Figure 1:
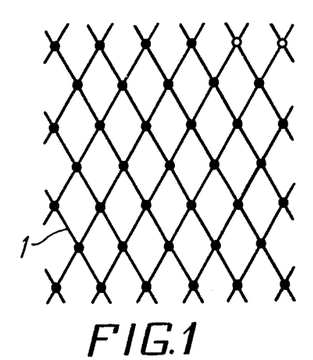
FIG. 1 is a metal net constituting the reinforcing base of the material, according to the invention.
Figure 2:
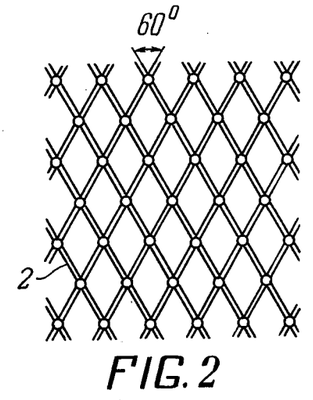
FIG. 2 is a polymer net constituting the reinforcing base of the material, according to the invention.
Figures 3, 4:
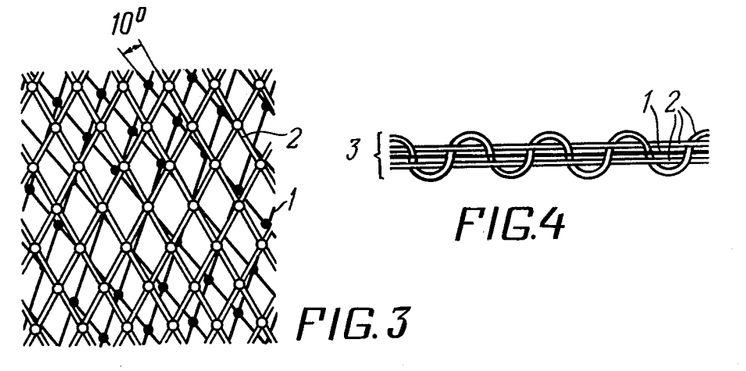
FIG. 3 is an embodiment of the arrangement of the net in the material.
FIG. 4 is a cross-sectional view of an embodiment of the reinforcing base of the material.

Reference being now made to the accompanying drawings, FIGS. 1, 2 and 3 illustrate the material for making bone endoprostheses to comprise a reinforcing base composed of three nets 1 and 2, the net 1 being made of a chemically and biologically inert metal and interposed between the two other nets 2 made of a chemically and biologically inert elastic polymeric material (FIG. 4).

The metal net 1 is made of a twisted multiple-strand titanium wire having a minimum diameter of 0.25 mm. The wires constituting the nets are joined together at the points of intersection by, for example, sintering at high pressure and elevated temperatures. Whenever it is necessary to make the material for making the metallic net 1 more rigid, use may be made of some other biologically and chemically inert alloys, such as stainless steel or Mo-Cr-Co alloys. If, on the contrary, one should desire to lessen the rigidity of the stock materials, use may be made of some chemically inert alloys featuring a lower modulus of elasticity, such as a Ti-Zr alloy.

The similar net 2 is made of twisted polymer fibres; a chemically and biologically inert polymeric material having a low modulus of elasticity is used for the purpose, such as Capron, Lavsan or Dacron. The wires of both metal and polymer nets form elementary diamond-shaped meshes featuring a vertex angle of 60°. In cases where flat-bone endoprostheses are made from the proposed material for, e.g. replacing defective cranial, scapular or iliac bones, more suitable is a mesh with a vertex angle equal to 90°; this imparts transverse isotropy to the material in the plane of location of the nets 1 and 2.

The thus prepared metal and polymer nets 1 and 2 are placed one upon the other and held together transversely by, for example, stitching with a polymer thread to a triplex sterically cross-linked network, viz., a web (FIG. 4). When the material is intended for endoprosthesis of diaphyseal bones, the metal and polymer nets should preferably be displaced with respect to each other in such a manner that the filaments forming the polymer nets 2 should be set at about 10° relative to respective wires of the metal net 1 in the parallel planes. When intended to be used for making flat bone prostheses, the material may have a different mutual orientation of the nets, that is, from 0° to 45°.

Then, the three-dimensional meshes resulting from superposing the nets 1 and 2 upon each other may be filled with an amorphous binding agent doped with an antiseptic, e.g., epoxy resin with a curing agent, both being produced according to routine process techniques. The embedding in the binder occurs at room temperature, whereupon it is exposed to airdrying for 24 hours.

Used as the binder may be polyethylene with a filling agent randomly spread thereover, such as graphite or any other suitable material biologically compatible with the live bone.

The reinforcing base of the endoprosthesis may also comprise another amount of the nets 1 and 2, e.g., one metal net per polymer net, or one metal net per three or four polymer nets, depending on the modulus of elasticity of the finished material and the modulus of elasticity of the metal the net 1 is made of. Should the modulus of elasticity of the metal of the net 1 be higher than that of titanium, the amount of the polymer nets 2 is to be increased. Basically, when titanium is used as the material for metal nets, the percentage of the metal reinforcing structure must be within 20 to 33 of the entire volume (or cross-sectional area) of the material, while the percentage of the polymeric reinforcements must range from 60 to 40, the rest being occupied by the binder, i.e., an approximate ratio between the metal, polymer and binder should be 1:2:1.

The volumetric ratio of the three principal components of the material is chosen proceeding from an assumption that the resultant material should feature an elastic behaviour and deformability approximating those of the bone tissue to be replaced, but be superior thereto in strength. Forasmuch as the nets 1, 2 of the reinforcing base have a definite predetermined orientation (depending on the purpose of the endoprosthesis), that renders the novel material markedly anisotropic, so that endoprostheses made therefrom acquire the same properties.

Flat bone endoprostheses may be made from stock produced by press-moulding of the metal and polymer nets 2 arranged in a number of interstitched plies along with the binder, by making therefrom plates 5 to 25 mm thick. In this case, polyethylene or polytetrafluoroethylene is more practicable to be used as the filler.

Figure 5:
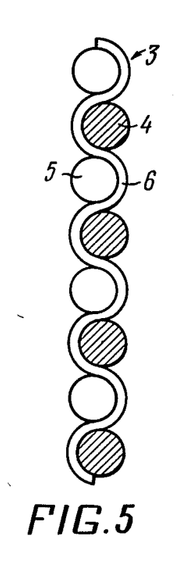
FIGS. 5, 6, 7 represent a cross-sectional view of an embodiment of the endoprosthesis made of the herein-proposed material.
Figure 6:
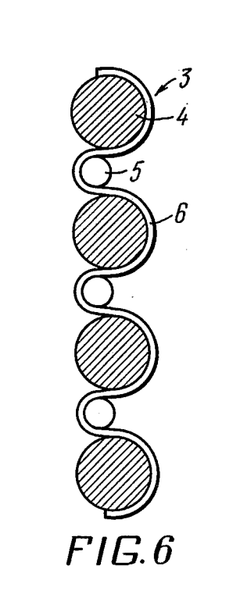
Figure 7:
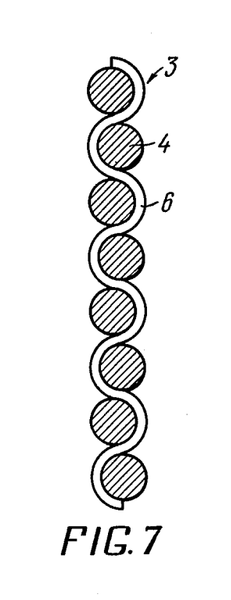
Figure 8:
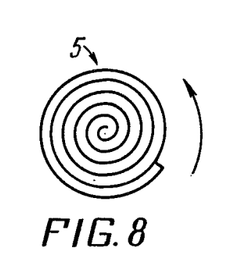
FIGS. 8, 9 show the hand of winding of spirals made of the herein-proposed material.
Figure 9:
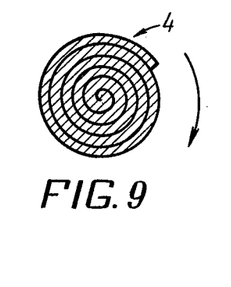

An endoprosthesis 3 shown in FIGS. 5, 6 and 7 is complicated and more resistant to heavy variable mechanical loads, hence, more suitable for making flat bone prostheses, as well as large diaphyseal bone prostheses for humans. Cross-sectionally, the endoprosthesis 3 is in fact a plurality of rows of L.H. and R.H. would spirals 4, 5 (FIGS. 8, 9) made of the material proposed herein. The spirals 4 and 5 of each row are interlinked through an element 6 made of the same material, while all the rows of the spirals 4 and 5 are embedded in a binding agent (not shown).

When intended for making flat-bone prostheses, the endoprosthesis 3 has adjacent rows of the spirals 4 and 5 arranged in mutually parallel planes; for making the endoprostheses of diaphyseal bones, all the spirals 4 and 5 are arranged lengthwise the longitudinal axis of the endoprosthesis. The plates formed by a row of spirals may be made, in different embodiments, as follows:

(a) the adjacent spirals of a row have an alternative hand of winding (FIGS. 5, 6);
(b) all the spirals in a row feature the same hand of winding (FIG. 7);
(c) the spirals 4 and 5 in a row differ in cross-sectional dimension (FIG. 6), e.g., in the case of the L.H. extremity prosthesis the cross-sectional dimension of the L.H. spirals 4 is two to five times that of the R.H. spirals 5, and vice versa for the R. H. extremity prosthesis. Flat-bone endoprostheses made of the plates of that type are distinguished by higher resistance to parallel shear.

Blanks for making flat-bone endoprostheses are prepared by laying a number of plates composed of spirals one upon another in several rows, embedding them in an amorphous binder with a curing agent and press-moulding of the resultant material.

The proposed endoprosthesis can also find application for correcting defects of long tubular bones. In this case, blanks made from plates of the types specified above are twisted into spirals (not shown) of two types 1 to 3.5 cm thick i.e., L.H. wound and R.H. wound. The thus prepared spirals are embedded in an amorphous binder doped with a persistent-action antibacterial agents. Thus, blanks or finished cylindrical endoprostheses are obtained for replacing either fragments or the entire diaphysis of bones exposed to relatively low loads, such as the humeral, ulnar, radial, clavicular bone, as well as carpal or pedal bones.

Whenever necessary, cylindrical blanks for endoprostheses may be subjected to mechanical treatment or fitting up for length or cross-sectional dimension.

Endoprostheses of major diaphyseal bones of the lower extremity, such as the femoral or tibial bone, are formed from the proposed material and correspond by their biomechanical characteristics to the natural prototypes, viz., the femoral and tibial bone of man, but are several times superior thereto as to their strength.

Figure 10:
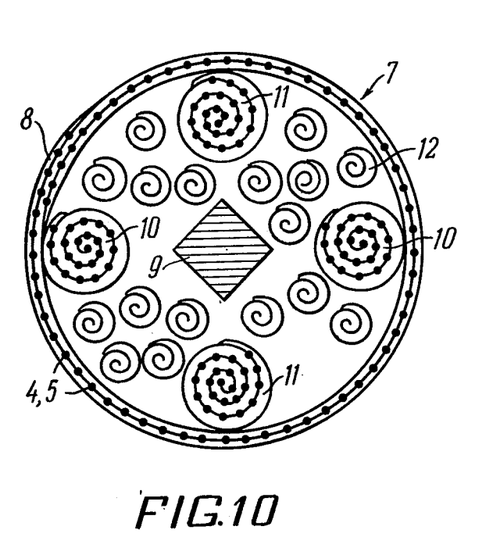
FIGS. 10, 11, 12 represent a cross-sectional view of some embodiments of the endoprosthesis for replacing major diaphyseal bones.

FIG. 10 illustrates one of the possible embodiments of the femoral-bone endoprosthesis. An endoprosthesis 7 of the femoral diaphysis is formed as a spiral sheath 8 with a central bearing rod 9 made of, for example, titanium and adapted for imparting greater rigidity to the endoprosthesis 7 and for interconnection with the end attachment assembly (not shown) of the latter intended for joining with the bone metaphyses. The interior space of the sheath 8 accommodates several spirals 10, 11 made of the proposed material and having a smaller perimeter. The sheath 8 and each of the spirals 10, 11 located thereinside are formed by a row of spirals 4 and 5 made of said network material and interconnected through the element 6 (FIGS. 5, 6) made of the same material. For the L.H. extremity prosthesis, they are made of plates made as specified in paragraph "a" hereinabove, twisted as a cylindrical rod 1 to 1.5 cm in diameter, the two spirals 10 located in the front and rear portions of the endoprosthesis being left-handed ones. Both spirals 11 located medially and laterally of the centre and having a diameter of up to 1.5 cm, are right-wound and are made of plates as specified in paragraph "c", wherein the transverse dimension of the left-hand would spirals 4 exceeds the transverse dimension of the right-hand wound spirals 5 (FIG. 6). Interposed between said four spirals 10, 11 are the left-hand wound spirals 12 of a smaller cross-sectional dimension made of the plates (FIG. 7) of the "b" type incorporating the right-hand spirals 5. The quantity of the spirals 12 is varible; thus, for the R.H. extremity endoprosthesis, the hand of winding of all said spirals 10, 11 and 12 is opposite, i.e., the R.H. extremity endoprostheses as to their construction are mirror-opposed with respect to the L.H. extremity endoprosthesis 7. The entire vacant space of the endoprosthesis 7 is occupied by the binding agent such as epoxy resin with a filler.

Figure 11:
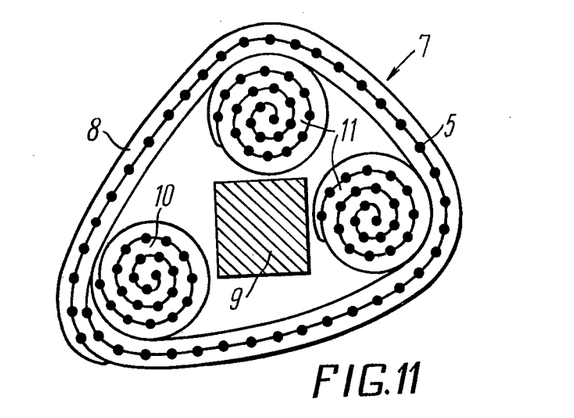
Figure 12:
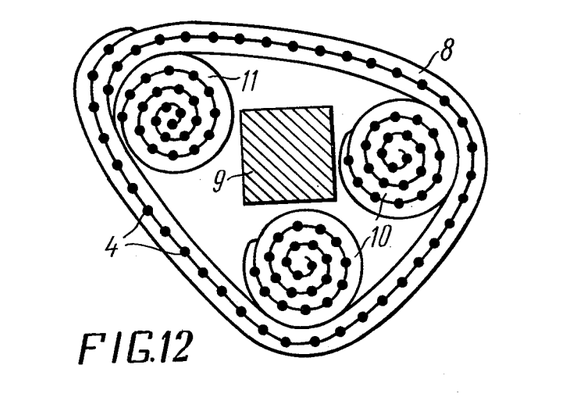

One of the possible embodiments of the tibial-bone endoprosthesis for humans is represented in FIGS. 11 and 12.

FIGS. 11 and 12 depict the endoprosthesis 7 of the tibial diaphysis wherein the outside spiral sheath 8 has cross-sectional shape approximating an oblique-angled triangle. The spirals 10 and 11 made of the proposed material are located at the vertices of said triangle, while at the centre thereof the metal bearing rod 9 is located, made of, for example, titanium. The rod 9 is also used for interconnection of the endoprosthesis 7 with the patient's bone. FIG. 11 illustrates the L.H. extremity endoprosthesis 7. The spiral 10 located at the vertex of the smaller oblique angle is left-hand wound. To make the spirals 10 it is desireable to use the plates of the "a" or "c" type, wherein the larger cross-sectional size spirals 4 are wound leftwards, whereas the spirals 5 of a smaller cross-sectional dimension are right-hand wound. The spirals 11 located at the remaining vertices of the triangle, as well as the spiral of the sheath 8, are wound rightwards and are likewise made from the plates of the "a" or "c" type. To render the endoprosthesis more compact, the space confined within the spirals 10 and 11 can be occupied by numerous left-hand wound spirals (not shown) of a much smaller cross-sectional dimension, made from the "a" type plates composed of right-hand wound spirals 5. The construction of the R.H. extremity endoprosthesis (FIG. 12) is similar to that disclosed above with the only difference that the hand of winding of all the spirals 8, 10, 11 of the endoprosthesis 7 is reversed.

Figure 13:
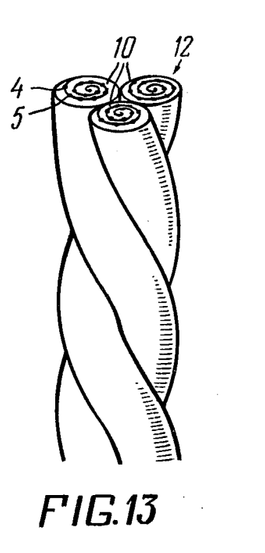
FIG. 13 is a longitudinal-section view of a spiral of the endoprosthesis, according to the invention.

FIG. 13 shows an embodiment of the spiral 12 of the endoprosthesis 7 which is twisted into a rope from the spirals 10 of a smaller cross-sectional size made of the "c" type plates.

What is claimed is:

1. A material for making bone endoprostheses, featuring a laminated structure and comprising: a reinforcing base made as a number of nets, some of which are of a chemically and biologically inert metal or alloy, while the other nets are of a chemically and biologically inert polymeric material; an antiseptic-doped binding agent occupying the whole space confined within said nets; the volumetric ratio between said metallic nets and the entire material being selected such that the modulus of elasticity of the material approximates that of the bone tissue.

2. A material as claimed in claim 1, wherein the wires of the nets form parallelogram-shaped meshes featuring an acute angle equal to 60°.

3. A material as claimed in claim 1, wherein the wires of the nets are set apart in parallel planes at a maximum angle of 10°.

4. A material as claimed in claim 1, wherein the volumetric ratio between the metal net and the entire implant is within 1:5 to 1:3.

5. A material as claimed in claim 1, wherein the binder is essentially epoxy resin with a curing agent.

6. A material as claimed in claim 1, wherein the binder is essentially polyethylene with graphite filler.

7. An endoprosthesis made of the material as claimed in claim 1, wherein it is essentially a plurality of rows of spirals wound from said network material and arranged lengthwise the axis of the endoprosthesis, each of the rows of spirals being interconnected by an element made of the network material, which embraces all the spirals, all the rows of said spirals of the endoprosthesis being embedded in a binder.

8. An endoprosthesis made of the material as claimed in claim 7, wherein the hand of winding of adjacent spirals in each of the rows alternates.

9. An endoprosthesis made of the material as claimed in claim 7, wherein the centres of the spirals in each row lie on a common imaginary straight line.

10. An endoprosthesis made of the material as claimed in claim 1, wherein it is shaped as a spiral sheath whose interior space accommodates a number of spirals arranged lengthwise said sheath, the perimeter of each of the spirals being less than that of the sheath, each of the spirals being cross-sectionally shaped as a row of spirals made of said network material and interlinked by an element made of the same material, and provision being made in the central zone of the sheath for a bearing rod arranged lengthwise the latter, while all the components of the prosthesis are embedded in a binder.

11. An endoprosthesis as claimed in claim 10, wherein the cross-sectional shape of the sheath approximates an oblique-angled triangle, while the spirals are located at the vertices of said triangle.

12. An endoprosthesis as claimed in claim 11, wherein the hand of winding of the spiral located at the vertex of the smaller oblique angle of said triangle is opposite to that of the spirals located at the remaining vertices of the triangle.

13. An endoprosthesis as claimed in claim 10, wherein each of the spirals enclosed in the sheath is twisted from a number of spirals of a smaller perimeter.

* * * * *